United States Patent [19]

Thompson

[11] Patent Number: 4,917,683
[45] Date of Patent: Apr. 17, 1990

[54] CANINE SEASONAL PANTIES

[76] Inventor: Kathaleen H. Thompson, 4389 Misty Morning Dr., Memphis, Tenn. 38115

[21] Appl. No.: 297,026

[22] Filed: Jan. 17, 1989

[51] Int. Cl.⁴ ..................... A61F 13/16; A01K 23/00
[52] U.S. Cl. ...................................... 604/387; 119/95
[58] Field of Search ..................... 604/358, 378, 385.1, 604/386, 387, 389, 390–394; 54/78, 79; 119/95, 143

[56] References Cited

U.S. PATENT DOCUMENTS

| | | | |
|---|---|---|---|
| 2,290,110 | 7/1942 | McGraw | 604/385.1 |
| 2,974,635 | 3/1961 | McDowell | 119/143 |
| 3,211,132 | 10/1965 | Hersh | 54/79 |
| 3,335,721 | 8/1967 | Gastwirth | 604/391 |
| 4,133,297 | 1/1979 | Denebeim | 119/143 |
| 4,182,331 | 1/1980 | Rodriguez | 119/95 |
| 4,577,591 | 3/1986 | Wesseldine | 604/398 |
| 4,813,949 | 3/1989 | O'Rourke | 119/95 |

FOREIGN PATENT DOCUMENTS

| | | | |
|---|---|---|---|
| 3132671 | 4/1982 | Fed. Rep. of Germany | 119/95 |
| 0577401 | 9/1924 | France | 119/143 |
| 0683622 | 6/1930 | France | 119/143 |
| 0963545 | 7/1950 | France | 604/385.1 |
| 2574286 | 6/1986 | France | 604/387 |
| 0943116 | 11/1963 | United Kingdom | 119/143 |

Primary Examiner—John D. Yasko
Assistant Examiner—Sharon Rose
Attorney, Agent, or Firm—John J. Mulrooney

[57] ABSTRACT

A garment made of one-piece of an absorbent pliable fabric for covering the hindquarter of a female dog has a pair of openings for the dog's rear legs, an opening for the dog's tail, an elastic band for encircling the dog's loin area, and snaps for closing the garment at the dog's point of rump.

6 Claims, 1 Drawing Sheet

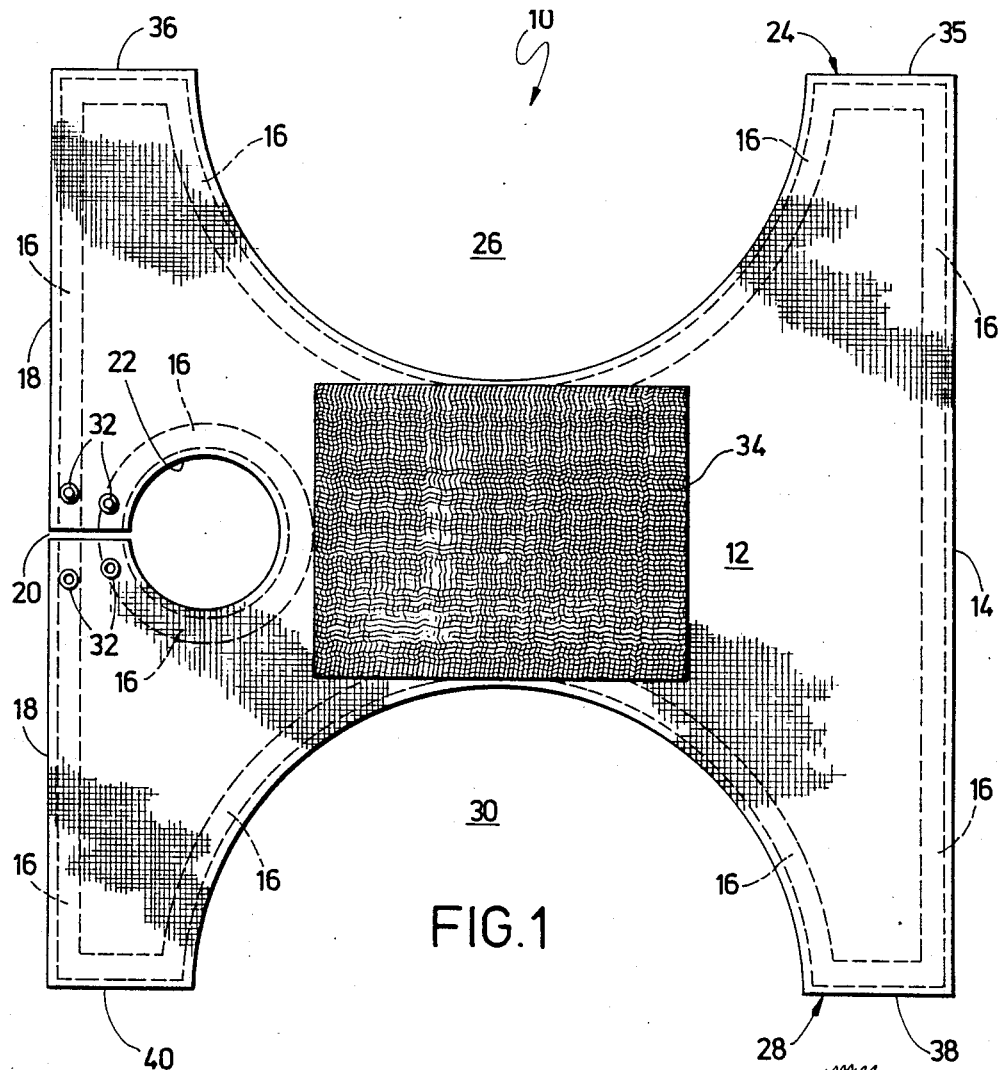
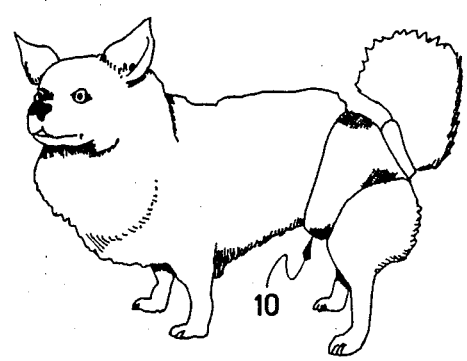
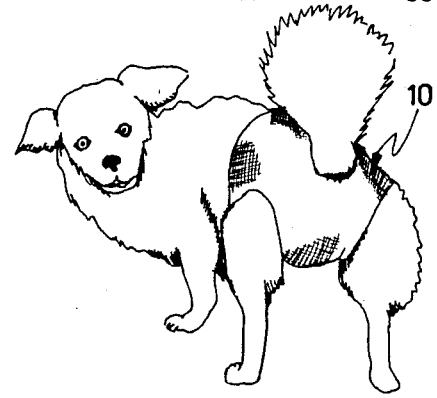
FIG.1
FIG.2
FIG.3

CANINE SEASONAL PANTIES

BACKGROUND OF THE INVENTION

This invention relates to articles of clothing for animals, and more particularly to panties useful on a canine bitch to prevent soiling or staining of clothing and furniture by the bitch's seasonal fluids.

Prior to this invention, canine garments useful for protecting against seasonal fluids comprised garments made of plastic inside and out, or plastic inside and cloth outside. The garment had a continuous elastic band which encircled the dog's loin area for the purpose of holding the garment in place. A disposable pad was used to absorb the seasonal fluids. These prior art garments did not function satisfactorily because, being made of plastic, they tended easily to slip off or slid out of place. The dog's tail had to be pushed or pulled through a tail opening, apparently at great discomfort to the dog. Finally, the disposable pad was an additional expense because it could not be reused. The prior art canine panties known to the inventor do not provide a garment designed for both protection against the seasonal fluids and comfort for the dog. The prior art garments do not provide a design having a fabric material which stays in place, gives better protection and is more comfortable. The prior designs do not provide for a garment which may be put on the dog without having to pull or push the dog's tail through a tail opening. The prior designs do not provide for canine panties having an inner absorbent, integral pad which gives better protection and which is washable with the garment to avoid the expense of purchasing disposable pads.

Therefore, an object of the invention is to provide improved canine seasonal panties.

Another object of the invention is to provide improved canine seasonal panties having a tail opening designed to wrap around the dog's tail.

Another object of the invention is to provide improved canine seasonal panties having a built-in absorbent pad.

Another object of the invention is to provide canine seasonal panties comprising an absorbent, pliable fabric material for the comfort of the dog.

Another object of the invention is to provide canine seasonal panties having a design including an elastic band and snap fasteners which aid in putting-on and taking-off the garment and in keeping the garment on the dog.

Another object of the invention is to provide canine seasonal panties having a French cut design for the leg openings.

Another object of the invention is to provide canine seasonal panties having a split and snap design for easier dressing and undressing.

SUMMARY OF THE INVENTION

The canine seasonal panties of the present invention comprise a single piece of absorbent, pliable fabric cut and sewn to have an elastic band designed to encircle the stomach area, a pair of leg openings having a French cut, a crotch area reinforced with an integral, absorbent pad, a tail opening, a slit extending from the tail opening to the edge of the garment and snaps on either side of the slit for closing the garment after the garment is put on the dog.

BRIEF DESCRIPTION OF THE DRAWING

FIG. 1 is a layout of the single piece of fabric, including the integral pad, used to make the invention garment before folding and stitching to make the canine seasonal panties.

FIG. 2 is a side view of the invention garment on a dog.

FIG. 3 is a rear view of the invention garment on a dog.

DESCRIPTION OF THE PREFERRED EMBODIMENT

Referring to the drawing, the canine seasonal panties of the present invention are generally designated by the reference numeral 10. The garment comprises a single piece of absorbent pliable, fabric 12, such as cotton which will conform to the shape of the dog and be comfortable to the touch. A bottom part 14 which will cover the dog's stomach section. A top part 18 which will cover the dog's back section 18 has a slit 20 which extends from top section 18 to a circular tail opening 22. Edge 24 of the fabric has a 180-degree arch 26 cut therein and edge 28 of the fabric has a 180-degree arch 30 cut therein. When the panties are assembled, these 180-degree arches will form a French cut design for the leg openings which will provide for a better fit and more comfort for the dog. Two pairs of snaps 32 are attached to the fabric 12 adjacent edge 18 and on each side of the slit 20. Absorbent padding 34 is stitched in the crotch area of the garment. Elastic or bias tape 16 is sewn along the edges of the garment as shown.

Referring to FIG. 1, for an example of how one size of the canine seasonal panties garment is constructed, the garment is made from a single piece of absorbent, pliable fabric 12 which is approximately 14"×16". The bottom or stomach arc section 14 and top or back arc section 18 are cut 12" wide straight across at edges 14 and 18. A distance of 2" from edges 14 and 18 along sides 24 and 28 are cut 180-degree arches 26 and 30, respectively. The top or back arc section 18 has a slit 20 at the midpoint of edge 18 which extends from edge 18 to a circular tail opening 22 which is cut approximately ½" from the crotch section and padding 34. After the padding 34 is stitched in the crotch of the garment, bias tape 16 is stitched along the bottom or stomach arc section 14, along the top or back arc section 18, around the tail opening 22 and leg opening sections 26 and 30 of the garment. The snaps 32 are attached adjacent to slit 20. With the garment turned inside out, the bottom or stomach left-hand side at part 35 is stitched to the top or back left-hand side at part 36. Then the bottom or stomach right-hand side at part 38 is stitched to the top or back right-hand side at part 40. The garment is completed when turned so the outside is the visible side.

It can be seen that the canine seasonal panties of the present invention provide a garment created with protection and comfort in mind. The panties are made of soft, absorbent, pliable fabric; and the crotch area contains a built-in absorbent pad to protect clothes, furniture and other objects which might be stained or soiled when the bitch is in season.

The canine seasonal panties of the present invention feature a tail opening which is designed to wrap around the dog's tail, and avoid the necessity of pulling or pushing the tail through an opening. The design of the garment plus the fabric provides comfort for the dog and gives better protection because it will better stay on the dog. The snap fasteners aid in easier use, thereby making the act of putting-on and taking-off the garment easier.

What is claimed is:

1. A garment for canine bitches comprising:
   an hourglass shaped portion having a generally rectangular top section having opposite side edges, a narrower middle portion forming a crotch section, and a generally retangular bottom section having opposite side edges;
   said top section and bottom section being connected to each other at their side edges to form a panty-like garment;
   said top section having a circular tail opening adapted to receive an animal's tail;
   an absorbent pad positioned in the crotch area adjacent to said circular tail opening;
   said top section being provided with a slit extended to said circular opening and bifurcating said top section; and
   snaps positioned on both sides of said slit for fastening said garment at the animal's back.

2. The garment of claim 1 wherein said front, middle and bottom portions comprise a single piece of pliable fabric and said absorbent pad is sewn thereto.

3. The garment of claim 1 wherein said circular opening is elastisized.

4. The garment of claim 1 wherein said middle portion has the shape of a French cut.

5. The garment of claim 1 wherein said middle portion is elastisized along the side edges.

6. The garment of claim 1 wherein the edges of said top and bottom sections are elastisized.

* * * * *